United States Patent [19]

Doi et al.

[11] 4,337,215
[45] Jun. 29, 1982

[54] PROCESS FOR PURIFYING 2-ACRYLAMIDO-2-METHYLPROPANESULFONIC ACID

[75] Inventors: Shunichi Doi; Masatake Kamogawa, both of Yokohama, Japan

[73] Assignees: Nitto Chemical Industry Co., Ltd.; Mitsubishi Rayon Co., Ltd., both of Tokyo, Japan

[21] Appl. No.: 8,114

[22] Filed: Jan. 31, 1979

[30] Foreign Application Priority Data

Feb. 9, 1978 [JP] Japan ................................. 53-13897

[51] Int. Cl.$^3$ .......................................... C07C 143/02
[52] U.S. Cl. ............................................. 260/513 N
[58] Field of Search ................................... 260/513 N

[56] References Cited

FOREIGN PATENT DOCUMENTS 2523616 2/1976 Fed. Rep. of Germany .
1090779 11/1967 United Kingdom .

*Primary Examiner*—Alan Siegel
*Attorney, Agent, or Firm*—Cushman, Darby & Cushman

[57] ABSTRACT

This disclosure relates to a process for the purification of 2-acrylamido-2-methylpropanesulfonic acid, which comprises dissolving said sulfonic acid in hydrous acetic acid of a water content of 3 to 80% by weight at 60° to 110° C. and subjecting the resulting solution to recrystallization. The purified product thus obtained is useful particularly as a starting material in preparing a high-molecular-weight polymer or copolymer.

8 Claims, No Drawings

PROCESS FOR PURIFYING 2-ACRYLAMIDO-2-METHYLPROPANESULFONIC ACID

BACKGROUND OF THE INVENTION

1. Field of the Invention

This invention relates to a purification process for the efficient preparation of high-purity 2-acrylamido-2-methylpropanesulfonic acid.

2. Description of the Prior Art

2-Acrylamido-2-methylpropanesulfonic acid (hereinafter referred to simply as AMPS) to be purified according to this invention is a known compound which is prepared by the methods described in U.S. Pat. Nos. 3,506,707 and 3,544,597, British Pat. No. 1,090,779, German Offenlegungsschrift No. 2,523,616, and Japanese Patent Publication 30,059/75.

In a preparative method typical of those described in the above patent publications, isobutene and fuming sulfuric acid are allowed to react in the presence of an excess of acrylonitrile, which is also used as reaction medium, and the resulting AMPS is allowed to precipitate directly from the reaction mixture. The crude crystals thus obtained are washed with acrylonitrile and, if necessary, recrystallized from a solvent.

Beside being used as an agent for improving the dyeing property of acrylic or other fibers, AMPS and its homologs can be polymerized to form useful homopolymers and copolymers. These polymers are useful as polyelectrolytes and are known to be usable as flocculant, dispersant, adhesive and fluidity regulator, and there are many patents in these fields.

The crude AMPS crystals as obtained by washing with a solvent the crystals precipitated directly from the reaction mixture may be used in some of the above-mentioned uses. However, in order to produce a polymer having a considerably high molecular weight, the crude crystals must be completely dissolved in a solvent and recrystallized therefrom.

For instance, the copolymer of AMPS and acrylamide for use as a mucilaginous material for papermaking and a flocculant must have a high molecular weight, and in order to produce such a high molecular weight copolymer, AMPS must have such a high purity as to be obtained by repeated recrystallization, otherwise no satisfactory result can be obtained.

The use of a copolymer of AMPS and acrylamide as a mucilaginous material for papermaking has been described in U.S. Pat. No. 3,772,142 and Japanese Patent Application Kokai (Laid-Open) Nos. 59,507/75 and 27,808/77.

Regarding the function of a mucilaginous material for papermaking, Japanese Patent Application Kokai (Laid-Open) No. 27,808/77, states that "this function is to enable fibers of a pulp and the like to be dispersed in water, and the most important point is whether or not the mucilaginous material added only in a small amount to a fiber slurry in sheet formation can sufficiently control the rate of drainage; the practical usefulness of a mucilaginous material in controlling the rate of drainage is evaluated in terms of anti-freeness which corresponds to the spinnability of an aqueous solution of said mucilaginous material, said spinnability corresponding also to the amount of mucilaginous material used per unit weight of pulp in practical papermaking". The values of both spinnability and anti-freeness, which are defined hereinafter, increase with an increase in purity of AMPS used as a starting material. The larger the said values, the higher the molecular weight of the copolymer and the more favorable the effect on papermaking.

In purifying AMPS by recrystallization from a solvent, the type of solvent-purification methods is limited because AMPS is soluble in only water, lower alcohols and dimethylformamide. Moreover, water tends to cause polymerization and decomposition of AMPS at temperatures 50° C. or more, while dimethylformamide is disadvantageous in that precipitation of crystals of AMPS is not easy and owing to its high boiling point the drying of precipitated crystals requires a long period of time. For these reasons, methanol seems to have been chiefly used as the solvent in conventional purification of AMPS by recrystallization, as described, for example, in British Pat. No. 1,090,779 and Japanese Patent Publication 30,059/75 in connection with compounds analogous to AMPS.

However, when using purified AMPS, which is obtained by a recrystallization method in which methanol is used as the solvent (hereinafter referred to simply as methanol method), the spinnability and anti-freeness of a copolymer thereof with acrylamide do not exceed certain values, even though the AMPS is repeatedly recrystallized. Moreover, in order to enhance the purity, it is important to wash the recrystallized product, and when it is intented to dissolve, for example, AMPS in methanol at the boiling point of methanol, recrystallize the solution at 20° C. and then wash the resulting crystals with the methanol to remove the mother liquor sufficiently, the final yield of crystals becomes as low as about 50% because the solubility of AMPS in methanol at room temperature is great. Further, methanol readily absorbs water because of its high hygroscopicity during the separation of crystals and other treatments. Since methanol of a high water content causes polymerization and decomposition of AMPS during purification, the methanol recovered for reuse must be sufficiently purified.

SUMMARY OF THE INVENTION

Since, as mentioned above, the methanol method has a number of problems and there is a limit in spinnability of the copolymer, a recrystallization method in which other solvents are used has been examined.

The present inventors, therefore, have added to water in which crude crystals of AMPS have been dissolved various organic solvents which are compatible with water but do not dissolve AMPS to precipitate AMPS crystals, and polymerized the AMPS crystals, after which the performance of the resulting copolymer has been evaluated. Consequently, it has been found that when acetic acid is used as the solvent, the spinnability and anti-freeness and somewhat improved. However, owing to the strong acidity (pH < 1) of an aqueous AMPS solution, polymerization proceeds simultaneously with the dissolution of AMPS crystals at 70° C., and even at 60° C. polymerization and decomposition proceed with the lapse of time, resulting in a marked decrease in the yield of recrystallized AMPS. It has been found that when crude crystals are dissolved in water at a temperature of 50° C. or less and then acetic acid is added thereto to recrystallize AMPS, it is necessary to use a large quantity of acetic acid in recovering AMPS crystals in a high yield.

In British Pat. No. 1,090,779 and German Offenlegungsschrift No. 2,523,616, a brief mention is made of the recrystallization of AMPS from acetic acid; however there is no description of detailed procedure. In this case, AMPS is hardly dissolved in acetic acid even at high temperatures. Therefore, it is natural for those skilled in the art to understand that the method of said British patent comprises first dissolving AMPS in water and then adding acetic acid thereto to precipitate crystals.

The present inventors have, therefore, conducted extensive studies on acetic acid as recrystallization solvent, taking the spinnability and anti-freeness of the copolymer as criteria and, as a result, have found that the recrystallization of AMPS from hydrous acetic acid as the solvent results in AMPS suitable for use in preparing a mucilaginous material for papermaking having a high spinnability and a high anti-freeness. It has further been found that both the yield of purified AMPS and the utilization efficiency of the solvent are extremely high and that AMPS is unexpectedly very stable in hydrous acetic acid.

According to this invention, there is provided a process for the purification of AMPS, which comprises dissolving said AMPS in hydrous acetic acid having a water content of 3 to 80% by weight at 60° to 110° C. and subjecting the resulting solution to recrystallization.

DETAILED DESCRIPTION OF THE INVENTION

As described hereinafter, AMPS is stable in the hydrous actic acid used in this invention over a wide dissolution temperature range, and hydrous acetic acid having a water content in a broad range of 3 to 80% by weight may be used, though the water content is preferably in the range of 5 to 40% by weight in view of the ease of operation, the yield of crystals, and the like.

AMPS is sparingly soluble in anhydrous acetic acid but is soluble in hydrous acetic acid containing a small amount of water. For example, the solubility of AMPS at 90° C. in hydrous acetic acid having a water content of 10% by weight (hereinafter referred to simply as percent) is more than 1.5 times that in boiling methanol. Moreover, the solubility in hydrous acetic acid at low temperatures is lower than in methanol. Thus, the yield of crystals in the process of this invention is higher than that in the methanol method. Since the solubility of AMPS in hydrous acetic acid containing less than 3% of water at room temperature is substantially zero, it is possible to obtain AMPS crystals in a substantially quantitative yield by dissolving crude AMPS in, for example, hydrous acetic acid having a water content of 10% and then adding to the solution anhydrous or glacial acetic acid or acetic anhydride to reduce the water content of the solution to less than 3% or distilling the solution to remove a half of the initial acetic acid in the form of 20% hydrous acetic acid from the system. Further, the use of the hydrous acetic acid of a water content is less than 3% to wash the recrystallized AMPS enables thorough washing with substantially no dissolution loss unlike the case of methanol, and hence facilitates the quality control.

With an increase in water content of hydrous acetic acid, the solubility of AMPS therein at low temperatures gradually increases and, hence, the yield gradually decreases. As the water content of hydrous acetic acid is increased to more than 40%, the stabilizing effect of acetic acid on AMPS decreases gradually, in addition to the increase in solubility at low temperatures and the decrease in temperature dependency of the solubility, so that it becomes impracticable to dissolve AMPS at too high a temperature, resulting in a great decrease in recrystallization yield. However, the decrease in yield with an increase in water content of hydrous acetic acid occurs only in the series of operations of dissolving AMPS and cooling the resulting solution to recrystallize AMPS, and such a decrease in yield can be avoided, so long as the AMPS remains stable, by the addition of anhydrous or glacial acetic acid or acetic anhydride or by distillation to reduce the water content of the solution as mentioned above; or by combining it with the repeated use of the mother liquor.

On the other hand, when the water content of hydrous acetic acid is less than 3%, the solubility of AMPS decreases rapidly and approaches nearly zero at room temperature. Therefore, it is desirable in respect of the recrystallization yield. However, the solubility at high temperatures is also low and hence an increased quantity of hydrous acetic acid becomes necessary to dissolve crude AMPS. Therefore, said low water content is not desired in industry.

Although the recrystallization yield increases with an increase in temperature for dissolution of crude AMPS, the dissolution temperature is in the range of 60° to 110° C., preferably 80° to 100° C., in view of both the stability of AMPS and the yield of crystals.

The thermal stability of AMPS contained in an amount of 20% in each of hydrous acetic acid, water and methanol at 70° C. (at the boiling point in the case of methanol) was estimated by measuring the residual double bond. The residual double bond decreases to 90% after one hour and to 40% after 5 hours, respectively, in the case of water, and to 97% after one hour in the case of methanol (containing 0.5% of water, the boiling point thereof being about 66° C.), whereas the residual double bond remains 100% even after 5 hours in the case of hydrous acetic acid containing 10% of water, indicating remarkable stability. In hydrous acetic acid containing 10% of water, no decrease in residual double bond is observed at 90° C. after one hour and even at 110° C. for 30 minutes. On the other hand, an aqueous solution of AMPS changes into a significantly viscous polymer solution after 10 minutes at 90° C. In the case of a saturated aqueous solution of AMPS, polymerization takes place at 70° C. as soon as the dissolution of crystals in completed. The thermal stability of AMPS in hydrous acetic acid remains substantially unchanged at a water content of 30%, and is gradually deteriorated at a water content exceeding 40%. When the water content exceeds 80%, the thermal stability is rapidly deteriorated and the residual double bond at 70° C. becomes approximately the same as in the case of aqueous solution. Therefore, the temperature for dissolution of AMPS in hydrous acetic acid having a water content of 80% is about 60° C. at maximum. A dissolution temperature of less than about 60° C. is substantially insignificant in aspect of the recrystallization yield.

As mentioned above, in the presence of water, acetic acid exhibits an excellent AMPS stabilizing effect, whereas such as effect cannot be observed with other solvents.

The large decrease in the residual double bond in an aqueous or methanolic AMPS solution seems to be because thermal decomposition, beside polymerization, of AMPS tends to take place. Particularly in the case of an aqueous AMPS solution the dissolution temperature must be as low as about 50° C. for fear of polymerization and decomposition. Therefore, it is difficult to obtain crystals in high yields from the aqueous solution by use of an organic solvent. In fact, an aqueous AMPS solution, in which the residual double bond has decreased to about 90%, shows an apparently increased viscosity and brings about not only a loss in yield but also a disadvantage of difficult separation of crystals by filtration, which results in adhesion of an increased amount of mother liquor to the crystals and hence requires a larger amount of a washing solvent to be used to remove the mother liquor than in usual cases.

The amount of hydrous acetic acid used is usually 2 to 7 times the weight of crude crystals, though may be varied depending on the water content of hydrous acetic acid and the temperature for dissolution of crude crystals. Since AMPS is very stable in hydrous acetic acid, the mother liquor can, if necessary, be re-used to further increase the yield of crystals and the utilization efficiency of the solvent.

As described above, the purification method of this invention provides AMPS crystals in high yield in the very stable state with neither polymerization nor decomposition. Moreover, a copolymer of this AMPS and acrylamide shows a spinnability as high as 40 to 50 mm and an anti-freeness as high as 65 to 70%, both of which exceed by about 30% the maximum values in the case of AMPS prepared by the methanol method. Therefore, the AMPS crystals provided by the process of this invention are sufficiently pure for the manufacture of a mucilaginous material for papermaking or a flocculant. It has surprisingly been found that when crude crystals of AMPS obtained under inadequate reaction conditions which show only a spinnability of less than 10 mm even after recrystallization from methanol and produce, when copolymerized with acrylamide, only a copolymer unsuitable for a flocculant or a mucilaginous material for papermaking, are recrystallized from hydrous acetic acid, the resulting crystals show a high spinnability and a high anti-freeness equivalent to those in the case of AMPS prepared under normal reaction conditions.

Although the reason for these superior properties of copolymer attained by use of AMPS obtained by the process of this invention, as compared with AMPS obtained by the methanol method, is yet to be elucidated, it seems probable that the impurities in the crude crystals adversely affecting these properties of copolymer are selectively converted to non-injurious substances by chemical reaction when heated with water in the hydrous acetic acid.

In Japanese Patent Publication 30,059/75, there is a description to the effect that a sulfate of the Ritter reaction product is occasionally formed as a by-product in preparing AMPS and this sulfate can be removed by simply washing the crude crystals with acetic acid. However, the present inventors have found that after having been stirred for several hours in anhydrous acetic acid with heating at 90° C., AMPS prepared under normal reaction conditions yields a copolymer having substantially the same properties as those of a copolymer obtained from untreated AMPS. It has also been found that the properties of a copolymer obtained from AMPS which had been treated with anhydrous acetic acid and recrystallized by the methanol method were substantially the same as those of a copolymer obtained from AMPS which had been subjected to only recrystallization by the methanol method. Therefore, in order to improve the spinnability and anit-freeness of the copolymer, it is necessary to purify the AMPS by dissolving completely in hydrous acetic acid with heating, and simple washing with acetic acid cannot achieve the object.

In the process of this invention, the starting material is crude AMPS crystals which have been obtained by washing precipitates from the reaction mixture obtained by any of the above-mentioned preparation methods, with the same solvent as used in the reaction, and drying the same. The water content of the hydrous acetic acid used is preferably 5 to 40%. Since the solubility of AMPS increases with an elevation in temperature, it is desirable to dissolve crude crystals in the hydrous acetic acid at a temperature as high as possible in order to increase the yield of recrystallized AMPS. However, in view of the stability of AMPS when heating it for a long period of time, a temperature of 90° C. is employed as standard in dissolving crude crystals. The quantity of the hydrous acetic acid required to completely dissolve the desired amount of AMPS therein at 90° C. depends on the water content. Where the hydrous acetic acid has a water content of 10%, it is used in an amount of about 4 to 5 times the weight of crude crystals. After the crude crystals have been completely dissolved by heating with stirring under the above conditions, the resulting solution is allowed to stand until it is cooled to about 10° to 20° C. to precipitate the crystals. The crystals are collected by filtration, washed twice with approximately the same quantity of acetic acid as the quantity of the crude crystals charged, and then dried.

PREFERRED EMBODIMENT OF THE INVENTION

This invention is further illustrated below in detail with reference to Examples. In the Examples, the performance characteristics of copolymers were tested in the following manner on a copolymer prepared from the AMPS crystals obtained and acrylamide.

Polymerization

In 900 cc of water were dissolved 15 g of AMPS and 85 g of acrylamide. After having been adjusted to pH 8, the solution was made up to 1,000 cc and charged into a polymerizer. To the polymerizer which had been thoroughly flushed with nitrogen were added 20 mg of potassium persulfate and 20 mg of dimethylaminopropionitrile. The polymerization was started at 35° C. and after 4 to 5 hours a maximum temperature of around 52° C. was attained. After 10 hours, the resulting polymer was discharged, allowed to cool, dried at 105° C. for 4 hours, and pulverized.

Spinnability (mm)

A 0.1% by weight aqueous solution of the dried polymer was prepared and the spinnability of the solution was measured in a constant temperature and humidity chamber at 20° C. and 65% RH in the following manner: A glass rod, 6 mm in diameter, was immersed in the solution to a depth of 10 mm and withdrawn at a rate of 500 mm/minute until the liquid thread was broken. The distance from the liquid level to the end of the glass rod was measured.

Anti-freeness (%)

To a 0.3% by weight slurry of a commercial NBKP (coniferous bleached kraft pulp) beaten to a Canadian standard freeness (JIS P 8121) of 300 ml was added 0.1% by weight (based on the pulp) of a copolymer. The drainage (V) of the resulting slurry was measured by means of a Canadian standard freeness tester and the anti-freeness was calculated by the following equation:

$$\text{Anti-freeness} = \frac{300 - V}{V} \times 100.$$

A higher anti-freeness is indicative of a higher effectiveness of the polymer used as a mucilaginous material for papermaking.

Viscosity (centipoise)

The viscosity of a 0.1% by weight aqueous solution of a copolymer was measured at 25° C. by using a Brookfield viscometer at 6 rpm.

The crude AMPS crystals used in the Examples (except Example 10) were prepared as shown below. Example of preparation of crude AMPS crystals.

Into a reactor equipped with a stirrer, a distillation column and a gas inlet tube was charged 100 parts by weight of acrylonitrile. To the reactor was added at 0° C. 18.8 parts by weight of 6% fuming sulfuric acid (which refers hereinafter to fuming sulfuric acid containing 6% of free $SO_3$). Into the resulting mixture was introduced 11.1 parts by weight of gaseous isobutene at a temperature of 50° C. or less. The reaction mixture was aged with stirring at 50° C. for one hour. After having been cooled to 20° C., crystals were collected, washed with approximately equal weight of acrylonitrile, and dried.

EXAMPLE 1

To 450 g of hydrous acetic acid of a water content of 10% were added 100 g of crude AMPS crystals. The mixture was heated with stirring at 90° C. to dissolve completely the crystals and stirred for a further 15 minutes at 90° C. The solution was then allowed to stand to precipitate crystals. The resulting slurry was further cooled below room temperature. One hour after the temperature of the slurry reached 15° C., the crystals were collected by filtration, washed twice with 100-g portions of acetic acid, and dried in a hot air drier at 60° C. to obtain 73 g of purified AMPS crystals. A copolymer was prepared using the purified crystals in the above-mentioned manner and the performance characteristics of the copolymer were determined in the abovementioned manner. The results were as shown in the Table.

The purified crystals obtained in the following Examples were subjected to copolymerization in the same manner as described above and the resulting copolymers were subjected to the same tests as above. The results were summarized in the Table.

EXAMPLE 2

To 300 g of hydrous acetic acid of a water content of 10% were added 100 g of crude AMPS crystals. The mixture was quickly heated with stirring at 110° C. to dissolve completely the crystals. The solution was then allowed to stand to precipitate crystals which were treated in the same manner as in Example 1 to obtain 80 g of purified AMPS crystals.

EXAMPLE 3

To 600 g of hydrous acetic acid having a water content of 10% were added 100 g of crude AMPS crystals, and the resulting mixture was heated at 60° C. with stirring to completely dissolve the crystals, after which the solution was allowed to stand to precipitate crystals. The precipitated crystals were treated in the same manner as in Example 1 to obtain 55 g of purified AMPS crystals.

EXAMPLE 4

To 700 g of hydrous acetic acid of a water content of 5% were added 100 g of crude AMPS crystals. The mixture was heated with stirring at 100° C. to dissolve completely the crystals. The solution was then allowed to stand to precipitate crystals. The precipitated crystals were treated in the same manner as in Example 1 to obtain 90 g of purified AMPS crystals.

EXAMPLE 5

To 200 g of hydrous acetic acid of a water content of 20% were added 100 g of crude AMPS crystals. The mixture was heated with stirring at 90° C. to dissolve the crystals completely. The solution was then allowed to stand to precipitate crystals. The precipitated crystals were treated in the same manner as in Example 1 to obtain 61 g of purified AMPS crystals.

EXAMPLE 6

The same solution of crude AMPS crystals in hydrous acetic acid as obtained in Example 1 was distilled at 70° C. to remove about half of the amount of the charged acetic acid under such distillation conditions that the water content of the remaining mother liquor became less than 3%. The resulting slurry was allowed to stand to be cooled at 15° C. and treated in the same manner as in Example 1 to obtain 95 g of purified AMPS crystals.

EXAMPLE 7

The same solution of crude AMPS crystals in hydrous acetic acid as obtained in Example 1 was cooled to 15° C., and 130 g of acetic anhydride was added slowly thereto. The temperature of slurry which rose above 15° C. owing to the exothermal reaction was lowered again to 15° C. The slurry was then treated in the same manner as in Example 1 to obtain 92 g of purified AMPS crystals.

EXAMPLE 8

Crude AMPS crystals were completely dissolved in hydrous acetic acid in the same manner as in Example 1. After addition of 500 g of glacial acetic acid, the resulting slurry was treated in the same manner as in Example 1 to obtain 90 g of purified AMPS crystals.

EXAMPLE 9

To 50 g of hydrous acetic acid having a water content of 80% were added 100 g of crude AMPS crystals, and the mixture was heated with stirring at 70° C. to dissolve the crystals completely, after which 750 g of glacial acetic acid was added thereto. The solution was then treated in the same manner as in Example 1 to obtain 90 g of purified AMPS crystals.

EXAMPLE 10

Crude AMPS crystals were obtained in a high yield in the same manner as in the aforementioned example of preparation of crude AMPS crystals, except that the free $SO_3$ content of the fuming sulfuric acid was increased to 40% (higher than usual content) to increase the yield of AMPS. The crude crystals wer recrystallized from methanol in the same manner as in Comparative Example 1 (described hereinafter). A copolymer prepared by using the thus purified crystals showed a spinnability of only 9 mm.

The crude crystals obtained above were recrystallized from hydrous acetic acid in the same manner as in Example 1. The spinnability and the anti-freeness of a copolymer prepared by using the thus purified crystals were 43 mm and 68%, respectively.

COMPARATIVE EXAMPLE 1

To 440 g of methanol were added 100 g of crude AMPS crystals. The mixture was heated with stirring at the boiling point of methanol to dissolve completely the crystals. The solution was stirred for a further 15 minutes at the same temperature and then allowed to stand to precipitate the crystals. The resulting slurry was further cooled to 10° C. After one hour, the precipitated crystals were collected by filtration, washed twice with 100-g portions of methanol, and dried in a hot air drier at 60° C. to obtain 58 g of purified AMPS crystals.

COMPARATIVE EXAMPLE 2

To 62 g of water were added 100 g of crude AMPS crystals. The mixture was heated with stirring at 50° C. to dissolve completely the crude crystals. After completion of the dissolution, the resulting aqueous solution was stirred for 15 minutes at 50° C. To the AMPS solution was added 1,300 g of glacial acetic acid and the mixture was cooled to 15° C. to precipitate the crystals. The precipitated crystals were treated in the same manner as in Example 1 to obtain 90 g of purified AMPS crystals.

COMPARATIVE EXAMPLE 3

A copolymer was prepared from the same crude AMPS crystals as used in Example 1 and other examples without purification. The polymer was viscous liquid and had a low molecular weight.

COMPARATIVE EXAMPLE 4

The same procedure as in Comparative Example 1 was repeated, except that the quantity of methanol was reduced to one-half and the methanolic AMPS solution in which about one-half of the crude crystals remained undissolved was refluxed for 3 hours and then treated in the same manner as in Comparative Example 1 to obtain 70 g of purified AMPS crystals.

COMPARATIVE EXAMPLE 5

To 400 g of anhydrous acetic acid were added 100 g of crude AMPS crystals. The mixture was heated with stirring at 90° C. for one hour, during which almost all of the crystals remained undissolved, and then treated in the same manner as in Example 1 to obtain quantitatively AMPS crystals. A copolymer obtained from the purified crystals was a polymer in the form of gel, which was evaluated after drying.

COMPARATIVE EXAMPLE 6

To 2500 g of hydrous acetic acid having a water content of 2% were added 100 g of crude AMPS crystals, and the mixture was heated with stirring at 90° C. to dissolve the crystals completely. The solution was allowed to stand to precipitate crystals. The precipitated crystals were treated in the same manner as in Example 1 to obtain 80 g of purified AMPS crystals.

COMPARATIVE EXAMPLE 7

To 900 g of hydrous acetic acid having a water content of 10% were added 100 g of crude AMPS crystals, and the mixture was heated with stirring at 50° C. to dissolve the crystals completely. The solution was thereafter allowed to stand to precipitate crystals. The precipitated crystals were then treated in the same manner as in Example 1 to obtain 40 g of purified AMPS crystals.

COMPARATIVE EXAMPLE 8

To 55 g of water were added 100 g of crude AMPS crystals. When the mixture was heated with stirring at 70° C., polymerization took place as soon as the crystals were dissolved completely.

TABLE

| | | | Purification conditions | | | | Properties of copolymer | | |
|---|---|---|---|---|---|---|---|---|---|
| | Type of solvent | Temp. for dissolution (°C.) | Water content of solvent (%) | | Amount of solvent required (Ratio to crystal) | Purification yield (%) | Viscosity (cps) | Spinnability (mm) | Anti-freeness (%) |
| | | | In dissolution | In crystallization | | | | | |
| Example 1 | Hydrous acetic acid | 90 | 10 | 10 | 4.5 | 73 | 395 | 45 | 71 |
| Example 2 | Hydrous acetic acid | 110 | 10 | 10 | 3 | 80 | 385 | 41 | 65 |
| Example 3 | Hydrous acetic acid | 60 | 10 | 10 | 6 | 55 | 385 | 40 | 63 |
| Example 4 | Hydrous acetic acid | 100 | 5 | 5 | 7 | 90 | 390 | 45 | 70 |
| Example 5 | Hydrous acetic acid | 90 | 20 | 20 | 2 | 61 | 390 | 44 | 70 |
| Example 6 | Hydrous acetic acid | 90 | 10 | 3 | 4.5 | 95 | 390 | 45 | 70 |
| Example 7 | Hydrous acetic acid (acetic anhydride added in later stage) | 90 | 10 | 3.8 | 5.8 | 92 | 390 | 43 | 68 |
| Example 8 | Hydrous acetic acid (glacial acetic | 90 | 10 | 4.7 | 9.5 | 90 | 395 | 45 | 70 |

TABLE-continued

| | | Purification conditions | | | | Properties of copolymer | | |
|---|---|---|---|---|---|---|---|---|
| | Type of solvent | Temp. for dissolution (°C.) | Water content of solvent (%) | | Amount of solvent required (Ratio to crystal) | Purification yield (%) | Viscosity (cps) | Spinnability (mm) | Antifreeness (%) |
| | | | In dissolution | In crystallization | | | | | |
| Example 9 | acid added in later stage) Hydrous acetic acid (glacial acetic acid added in later stage) | 70 | 80 | 5 | 8 | 90 | 390 | 45 | 70 |
| Example 10 | Hydrous acetic acid | 90 | 10 | 10 | 4.5 | — | 390 | 43 | 68 |
| Comparative Example 1 | Methanol | ca.66 | — | — | 4.4 | 58 | 370 | 32 | 51 |
| Comparative Example 2 | Water-acetic acid | 50 | 100 | 5 | 13(Acetic acid) | 90 | 375 | 35 | 55 |
| Comparative Example 3 | Not purified | | | | | Not measurable | | | |
| Comparative Example 4 | Methanol | ca.66 | — | — | 2.2 | 70 | 320 | 20 | 40 |
| Comparative Example 5 | Acetic acid | 90 | 0 | 0 | 4 | 99 | 200 | 8 | — |
| Comparative Example 6 | Hydrous acetic acid | 90 | 2 | 2 | 25 | 80 | 390 | 45 | 70 |
| Comparative Example 7 | Hydrous acetic acid | 50 | 10 | 10 | 9 | 40 | 375 | 36 | 57 |
| Comparative Example 8 | Water | 70 | 100 | — | — | Not measurable | | | |

What is claimed is:

1. A process for purifying 2-acrylamido-2-methylpropanesulfonic acid, which comprises dissolving crystals of 2-acrylamido-2-methylpropanesulfonic acid in hydrous acetic acid having a water content of 3 to 80% by weight at 60° to 110° C. and subjecting the resulting solution to recrystallization.

2. A process according to claim 1, wherein the weight ratio of the hydrous acetic acid to the crystals of 2-acrylamido-2-methylpropanesulfonic acid is from 2/1 to 7/1.

3. A process according to claim 1 or 2, wherein the water content of the hydrous acetic acid is 5 to 40% by weight.

4. A process according to claim 1 or 2, wherein the temperature for the dissolution of crystals is 80° to 100° C.

5. A process according to claim 1, wherein after dissolving the crystals of 2-acrylamido-2-methylpropanesulfonic acid in the hydrous acetic acid, the water content of the hydrous acetic acid is reduced by adding acetic anhydride or glacial acetic acid, thereby recrystallizing 2-acrylamido-2-methylpropanesulfonic acid.

6. A process according to claim 1, wherein after dissolving the crystals of 2-acrylamido-2-methylpropanesulfonic acid in the hydrous acetic acid, the water content of the hydrous acetic acid is reduced by distillation, thereby recrystallizing 2-acrylamido-2-methylpropanesulfonic acid.

7. A process according to claim 1, wherein the mother liquor from which the crystals have been separated is re-used as the solvent.

8. A process according to claim 1 wherein the solution is subjected to recrystallization by cooling the solution.

* * * * *